(12) United States Patent
Nakamura et al.

(10) Patent No.: US 8,338,108 B2
(45) Date of Patent: Dec. 25, 2012

(54) AGENT FOR PROMOTING THE PRODUCTION OF THIOREDOXIN

(75) Inventors: Hajime Nakamura, Kyoto (JP); Junji Yodoi, Kyoto (JP); Yuma Hoshino, Kyoto (JP)

(73) Assignees: Kyoto University, Kyoto (JP); Nippon Zoki Pharmaceutical Co., Ltd., Osaka (JP)

( * ) Notice: Subject to any disclaimer, the term of this patent is extended or adjusted under 35 U.S.C. 154(b) by 368 days.

(21) Appl. No.: 12/225,415

(22) PCT Filed: Mar. 29, 2007

(86) PCT No.: PCT/JP2007/056827
§ 371 (c)(1),
(2), (4) Date: Nov. 4, 2008

(87) PCT Pub. No.: WO2007/114230
PCT Pub. Date: Oct. 11, 2007

(65) Prior Publication Data
US 2010/0021431 A1    Jan. 28, 2010

(30) Foreign Application Priority Data
Mar. 30, 2006    (JP) .................................. 2006-093602

(51) Int. Cl.
*C12Q 1/68* (2006.01)
(52) U.S. Cl. .......................................... 435/6.16; 435/5
(58) Field of Classification Search .................. None
See application file for complete search history.

(56) References Cited

U.S. PATENT DOCUMENTS

| | | | |
|---|---|---|---|
| 6,165,515 A * | 12/2000 | Matsuyama et al. | 424/520 |
| 6,616,515 B2 * | 9/2003 | Dwyer | 451/65 |
| 7,148,012 B2 * | 12/2006 | Nishioka | 435/6 |
| 7,238,487 B2 * | 7/2007 | Nishioka | 435/6 |
| 7,425,547 B2 * | 9/2008 | Roberts et al. | 514/46 |
| 7,435,547 B2 * | 10/2008 | Nishioka | 435/6 |
| 2006/0194797 A1 * | 8/2006 | Takeuchi | 514/224.2 |

FOREIGN PATENT DOCUMENTS

| | | |
|---|---|---|
| JP | A-53-101515 | 9/1978 |
| JP | A-55-087724 | 7/1980 |
| JP | A-01-265028 | 10/1989 |
| JP | A-02-028119 | 1/1990 |
| JP | A-07-097336 | 4/1995 |
| JP | A-08-291077 | 11/1996 |
| JP | A-10-194978 | 7/1998 |
| JP | A-11-080005 | 3/1999 |
| JP | A-11-139977 | 5/1999 |
| JP | A-2000-016942 | 1/2000 |
| JP | A-2001-058949 | 3/2001 |
| JP | A-2001-058950 | 6/2001 |
| JP | A-2001-322929 | 11/2001 |
| JP | A-2003-336034 | 11/2003 |
| JP | A-2004-300146 | 10/2004 |
| JP | A-2005-060408 | 3/2005 |
| WO | WO 2004/039383 A1 | 5/2004 |
| WO | WO 2005/021518 * | 3/2005 |

OTHER PUBLICATIONS

Okada et al., "Neurotropin Increases in Vitro Life Span of Human Fibroblasts," Mechanisms of Aging and Development, 35, pp. 133-143, 1986 Elsevier Scientific Publishers Ireland Ltd.
Oct. 12, 2010 Chinese Office Action issued in Application No. 200780011408.7 (with Translation).

* cited by examiner

*Primary Examiner* — Doug Schultz
(74) *Attorney, Agent, or Firm* — Oliff & Berridge, PLC

(57) ABSTRACT

A novel pharmaceutical application of an extract from a vaccine virus-inoculated and inflamed tissue and relates to a thioredoxin production promoting agent containing the extract as an active ingredient. The extract has an excellent thioredoxin production promoting action against an oxidative stress caused by a stimulus by such as a tobacco smoke extract or hydrogen peroxide and showed a significant lung cell protective effect. Therefore, the pharmaceutical of the invention containing the extract as an active ingredient is highly useful as a preventive or therapeutic agent for a chronic obstructive lung disease considered to be mainly caused by a continuous oxidative stress such as chronic smoking and the pharmaceutical with less side effects and high safety.

7 Claims, 5 Drawing Sheets

AGENT FOR PROMOTING THE PRODUCTION OF THIOREDOXIN

TECHNICAL FIELD

The present invention relates to a novel medicinal application of an extract from inflamed tissues inoculated with vaccinia virus, and more particularly, relates to an agent containing an extract from inflamed tissues inoculated with vaccinia virus as an active ingredient for promoting the production of thioredoxin.

BACKGROUND ART

When a living body is exposed to various stresses such as exposure to environmentally harmful substances including ultraviolet ray or fine particle and inflammation caused by viral or bacterial infection, active oxygen species are produced in the cells and protein and gene are oxidized and disordered. Therefore, a living body has a system where redox response is basically a defensive mechanism against active oxygen species and one of the representative examples thereof is a thioredoxin system.

Thioredoxin has been found as a coenzyme which donates hydrogen ion to ribonucleotide reductase which is an essential enzyme for the DNA synthesis of *Escherichia coli*. Thioredoxin has an active site of -Cys-Gly-Pro-Cys- and is an intracellular oxidation-reduction controlling factor wherein a reduction type which forms dithiol (—SH—SH) and an oxidation type which forms a disulfide (S—S) bond between two cysteine residues are present.

It has been made clear already that thioredoxin is induced by ultraviolet ray, radioactive ray, oxidizing agent, infection of virus, ischemic reperfusion injury and administration of anticancer agent. It has been reported that thioredoxin induced by various stresses extinguishes singlet oxygen or hydroxyl radical solely and also acts in living body as an antioxidant which extinguishes active oxygen species by a cooperative action with peroxyredoxin whereby thioredoxin controls activity of transcription factor adjusting various gene expressions and signal transmitting molecules in cells. Accordingly, it is expected that, when thioredoxin is induced, then cells, tissues, organs, etc. are able to be protected from a morbid state on the basis of various oxidation-reduction phenomena caused in the cells or a previous stage thereof. And, therefore, studies for substances inducing thioredoxin have been developed already and, for example, there is a disclosure for isoprenoid compounds as an inducing substance (refer to the Patent Document 1).

As one of the diseases and morbid states caused by imbalance of the above-mentioned oxidation/antioxidant or redox state, there is a lung disease including chronic obstructive pulmonary disease (COPD), etc. COPD is a disease where a morbid state is a persistently clogged state of airway caused by sticking of sputum in one's throat, swelling of bronchus (chronic bronchitis) and destruction of pulmonary alveoli (pulmonary emphysema) as a result of chronic inflammation in airway or peripheral lung tissues by inhalation of toxic fine particles and its biggest cause is smoking. In cigarette smoke, a lot of oxidant is contained and the lung is in a state of being exposed to oxidation stress. Accordingly, thioredoxin which has been known to have anti-inflammatory and cytoprotective actions is suggested to suppress the tissue injury and inflammation by smoking. In fact, it has been reported that, in healthy smokers, concentration of thioredoxin in blood is significantly high as compared with nonsmokers and it is likely that an increase in production of thioredoxin acts as a protective mechanism against chronic smoking which is a persistent oxidation stress. From such a viewpoint, it is appropriate to use thioredoxin as a therapeutic strategy and it has been disclosed already that thioredoxin is effective as a preventive or treating agent for chronic obstructive pulmonary diseases (refer to the Patent Document 2).

Disclosed pharmacological activity regarding extracts from inflamed tissues inoculated with vaccinia virus includes the following: analgesic, sedative, anti-stress and anti-allergic actions (refer to the Patent Document 3); immune stimulation, anticancer and cirrhosis inhibition actions (refer to the Patent Document 4); a therapeutic effect for idiopathic thrombocytopenic purpura (refer to the Patent Document 5); therapeutic effects for post-herpetic neuralgia, cerebral edema, dementia, spinocerebellar degeneration and the like (refer to the Patent Document 6); therapeutic effects for Raynaud's disease, diabetic neuropathy, sequelae of subacute myelo-optic neuropathy and the like (refer to the Patent Document 7); kallikrein production inhibition and peripheral circulatory disturbance amelioration actions (refer to the Patent Document 8); bone atrophy amelioration action (refer to the Patent Document 9); nitric oxide production inhibition action effective in the treatment of septicemia and endotoxin shock (refer to the Patent Document 10); a curative effect for osteoporosis (refer to the Patent Document 11); a curative effect for AIDS based upon inhibition actions for Nef action and chemokine production (refer to the Patent Documents 12 and 13); a therapeutic effect for ischemic diseases such as cerebral infarctions (refer to the Patent Document 14); therapeutic effect for fibromyalgia (refer to the Patent Document 15); therapeutic effect for infectious diseases (refer to the Patent Document 16) and the like.

The Patent Document 1: Japanese Patent Laid-Open Publication No. 2001-322929
The Patent Document 2: Japanese Patent Laid-Open Publication No. 2005-60408
The Patent Document 3: Japanese Patent Laid-Open Publication No. S53-101515
The Patent Document 4: Japanese Patent Laid-Open Publication No. S55-87724 (pages 3, 5 and 6 in particular)
The Patent Document 5: Japanese Patent Laid-Open Publication No. H01-265028 (pages 1 and 2 in particular)
The Patent Document 6: Japanese Patent Laid-Open Publication No. H01-319422 (pages 3 and 4 in particular)
The Patent Document 7: Japanese Patent Laid-Open Publication No. H02-28119 (page 3 in particular)
The Patent Document 8: Japanese Patent Laid-Open Publication No. H07-97336 (page 4 in particular)
The Patent Document 9: Japanese Patent Laid-Open Publication No. H08-291077
The Patent Document 10: Japanese Patent Laid-Open Publication No. H10-194978
The Patent Document 11: Japanese Patent Laid-Open Publication No. H11-80005 (pages 2 and 3 in particular)
The Patent Document 12: Japanese Patent Laid-Open Publication No. H11-139977
The Patent Document 13: Japanese Patent Laid-Open Publication No. 2000-336034 (pages 2 and 3 in particular)
The Patent Document 14: Japanese Patent Laid-Open Publication No. 2000-16942
The Patent Document 15: International Patent Publication WO 2004/039383
The Patent Document 16: Japanese Patent Laid-Open Publication No. 2004-300146

DISCLOSURE OF THE INVENTION

Problems that the Invention is to Solve

An object of the present invention is to provide a substance which has antioxidant, anti-inflammatory and cytoprotective actions and promotes the production of thioredoxin which plays an important role as an oxidation-reduction controlling factor in the cells. Further object is to provide a drug containing said substance as an effective ingredient and being effective, with high safety, in prevention or treatment of chronic obstructive pulmonary diseases.

Means for Solving the Problems

As a result of intensive studies, the present inventors have found that an extract of inflamed tissues inoculated with vaccinia virus has an excellent promoting action in production of thioredoxin, shows a protective action for pulmonary cells and is useful as a preventive or treating agent for chronic obstructive pulmonary diseases whereby the present invention has been achieved.

Advantages of the Invention

Since an extract of inflamed tissues inoculated with vaccinia virus has an excellent pharmacological action to promote the production of thioredoxin against oxidation stress caused, for example, by chronic smoking and to show a pulmonary cell protective action, the drug of the present invention containing the same as an effective ingredient is highly useful as a safe drug without problems such as adverse action.

BEST MODE FOR CARRYING OUT THE INVENTION

Figure 1:
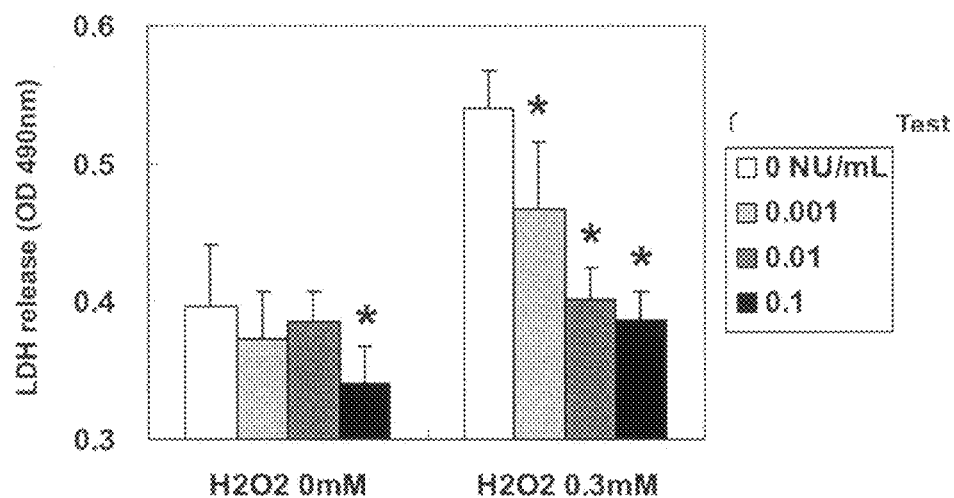
FIG. 1 is the result when a cytoprotective action of the extract of inflamed tissues inoculated with vaccinia virus according to the present invention to stimulation by hydrogen peroxide and serum-free stimulation was investigated.

With regard to an extract of inflamed tissues inoculated with vaccinia virus used for the drug of the present invention, there have been various reports for physiologically active substances produced in inflamed tissues inoculated with vaccinia virus, for a method of extracting said substance from morbid tissues, for a pharmacological activity thereof, etc. as mentioned above (the above Patent Documents 3 to 16, etc.).

A pharmaceutical preparation of an extract from inflamed cutaneous tissues of rabbits inoculated with vaccinia virus is sold in market. As described in pages 2585 to 2587 of *Ethical Drugs in Japan* [(2006 year edition), edited and published by Japan Pharmaceutical Information Center], the preparation is a drug containing a non-proteinous active substance extracted and isolated from inflamed cutaneous tissues of rabbits inoculated with vaccinia virus has been allowed to use for low back pain, neck-shoulder-arm syndrome, symptomatic neuralgia, periarthritis scapulohumeralis, arthritis deformans, pruritis caused by dermatoses (eczema, dermatitis and urticaria), allergic rhinitis, sequelae of subacute myelo-optico-neuropathy (coldness, pain and paresthesia/dysesthesia) and postherpetic neuralgia. Subcutaneous, intramuscular and intravenous injections, as well as tablets, have received manufacturing approval and are sold as ethical drugs.

An extract from inflamed tissues inoculated with vaccinia virus used for the drug of the present invention is a non-proteinous biofunction-regulating substance which is extracted from an inflamed tissues inoculated with vaccinia virus as described above. The pharmaceutical preparations of an extract isolated from inflamed cutaneous tissues of rabbits inoculated with vaccinia virus as listed in the above *Ethical Drugs in Japan* have received drug manufacturing approval and is commercially available. Moreover, the various extracts from inflamed tissues inoculated with vaccinia virus described in literature such as the patent publications mentioned above may be employed in the present invention, for which the production method, preferable dose and the like are also explained in the literature.

An extract from inflamed tissues inoculated with vaccinia virus used for the drug of the present invention can be obtained by inoculating an animal with vaccinia virus, finely cutting and crushing tissues, adding an extracting medium thereto and removing tissue fragments. And then, deproteinization is performed and the deproteinized solution is adsorbed by an adsorbent and then the adsorbed component is extracted.

An extract isolated from inflamed tissues inoculated with vaccinia virus can be produced, for example, according to the following process.

(a) Cutaneous tissues or the like are collected from rabbits, mice, etc. inoculated with vaccinia virus, and the finely cut tissues is crushed. An extracting medium such as water, phenol water, saline or phenol-added glycerin water is added, and then an extracted fluid (filtrate or supernatant) is obtained by filtration or centrifugation.

(b) The pH of the extracted fluid is made acidic and it is heated for deproteinization. The deproteinized solution is subsequently made alkaline and heated, after which it undergoes filtration or centrifugation.

(c) The obtained filtrate or supernatant is made acidic, then adsorbed by an adsorbent such as activated carbon or kaolin.

(d) An extracting solvent such as water is added to the adsorbent, the pH is made alkaline and the adsorbed component is eluted, thereby obtaining an extract from inflamed tissues inoculated with vaccinia virus. Thereafter, the eluate can be suitably freeze-dried or evaporated to dryness under reduced pressure to make dried materials.

As an animal which are infected with vaccinia virus for preparing the inflamed tissues by inoculation of vaccinia virus, animals which may infected with vaccinia virus, for example, rabbits, cows, horses, sheep, goats, monkeys, rats, mice or the like can be used. The preferred inflamed tissues are the inflamed rabbit skins.

The inflamed tissues are removed and finely cut, and made into an emulsified suspension by adding 1 to 5 times as much extracting solvent thereto. Examples of the extracting solvent applicable are distilled water, physiologically saline solution, weakly acidic to weakly basic buffers, etc. If necessary, stabilizers such as glycerol, antibacterial/antiseptic agents such as phenol, inorganic salt such as sodium chloride, potassium chloride or magnesium chloride may be added thereto. At that time, the extraction can be facilitated with a treatment by means of freezing/melting, ultrasonic waves, cell membrane dissolving enzymes or surface-active agents to cause cell destructions.

The resulting milky extract is filtered or centrifuged to remove tissue residues and then proteins are removed therefrom. Removal of proteins can be carried out by known methods, for example, heating, treatments with protein denaturing agents such as acids, bases, urea, guanidine, organic solvents such as acetone, surface-active agents, etc., isoelectric precipitation, salting-out and the like. Then the precipitated proteins are removed by usual means for removing insoluble matters, for example, filtration using filter paper (cellulose, nitrocellulose, etc.), glass filter, Celite or a Seitz filter, ultrafiltration, centrifugation and the like.

The obtained extraction containing active ingredients is adjusted to an acidic pH, preferably to pH 3.5-5.5, by acids such as hydrochloric acid, sulfuric acid and hydrobromic acid, and is adsorbed with an adsorbent. As an usable adsorbent, activated charcoal, kaolin, etc. may be employed. The adsorbents may be added to the extract followed by stirring or the extract may be passed through a column filled with the adsorbents whereby active ingredients can be adsorbed. In the case of adding the absorbent into the extracted solution, the absorbent absorbing the active ingredients can be separated by removing the solvent by filtration, centrifugation and the like.

To elute the active ingredients from the adsorbents, an eluting solvent is added to the adsorbents and eluted at room temperature or with heating to some extent or with stirring. The adsorbents may be removed by conventional means such as filtration and centrifugation to complete the elution. As a usable eluting solvent, water, methanol, ethanol, isopropanol or a mixture thereof which is adjusted to basic pH may be employed. Preferably, water adjusted to pH 9-12 can be used.

The extract (eluted solution) produced as above can be prepared to desired formulations for raw materials or medicines. For example, the solution is adjusted to neutral pH to prepare raw materials of drugs, and may be adjusted to desired concentrations by condensation or dilution. Furthermore, in order to prepare an injection, the solution may be prepared to an isotonic solution as same as saline. The solution may be prepared to solid preparations available for raw materials of tablets, etc. by concentration to dryness or lyophilization.

As a method of administration to a patient, oral and other administrations such as subcutaneous, intramuscular and intravenous administrations may be used. The dose is to be suitably decided depending upon the kind of an extract from inflamed tissue inoculated with vaccinia virus while the dose which is approved in the commercially available preparation according to the above "Drugs in Japan, Ethical Drugs" (page 2585) is, principally, 16 NU per day and 3.6-7.2 NU per day by oral administration and by injection, respectively. However, the dose may be appropriately increased or decreased depending upon the type of the disease, degree of seriousness, individual difference in the patients, method of administration, period of administration, etc. (NU: Neurotropin unit. Neurotropin unit is defined by $ED_{50}$ value of analgesic effect measured by a modified Randall-Selitto method using SART-stressed mice. The SART-stressed mice are chronic stressed animals showing a lowered pain threshold than a normal animal. One NU indicates the activity of 1 mg of analgesic ingredients in Neurotropin preparations when the $ED_{50}$ value is 100 mg/kg of the preparation.)

As hereunder, examples of the process for producing the extract of inflamed tissues inoculated with vaccinia virus and novel pharmacological action of the extract of the present invention or, in other words, results of pharmacological tests concerning a promoting action for thioredoxin production and a preventive/therapeutic action for COPD will be shown although the present invention is not limited by the description of those Examples at all.

EXAMPLES

Example 1

Skins of healthy adult rabbits were inoculated with vaccinia virus to cause inflammation. The inflamed skins were removed, finely cut and phenol water was added thereto. The mixture was filtered with pressure, and the resulting filtrate was adjusted to pH 5 with hydrochloric acid and then heated at 90-100° C. for 30 minutes. Proteins were removed by filtration, the filtrate was adjusted to pH 9 with sodium hydroxide, further heated at 90-100° C. for 15 minutes and filtered. The filtrate was adjusted to about pH 4.5, stirred for 2 hours after adding 2% of activated charcoal, and centrifuged. The resulting activated charcoal was mixed with water, adjusted to pH 10 with sodium hydroxide, stirred at 60° C. for 1.5 hours and centrifuged to give a supernatant. The activated charcoals precipitated by centrifugation were mixed with water, adjusted to pH 11 with sodium hydroxide, stirred at 60° C. for 1.5 hours and centrifuged to give a supernatant. Both of the supernatants obtained were combined and neutralized with hydrochloric acid to give an extract from inflamed tissue inoculated with vaccinia virus. In the following pharmacological studies, the extract was adjusted to appropriate concentrations to be used.

Example 2

Skins of healthy adult rabbits were inoculated with vaccinia virus to cause inflammation. The inflamed skins were aseptically removed, finely cut and phenol-added glycerin water was added thereto. The mixture was ground using a homogenizer to prepare an emulsion. The emulsion was filtered with centrifugation, and the resulting filtrate was adjusted to pH 4.8-5.5 with hydrochloric acid, heated at 100° C. with a steam flow and then filtered. The filtrate was further filtered with Seitz filter, adjusted to pH 9.2 with sodium hydroxide, heated at 100° C. and filtered. The filtrate was adjusted to pH 4.5, stirred for 1-5 hours after adding 1.5% of activated charcoal, and filtered. The activated charcoal was mixed with water, adjusted to pH 9.4-10 with sodium hydroxide, stirred for 3-5 hours and filtered. The resulting filtrate was neutralized with hydrochloric acid and dried in vacuo.

Example 3

Skins of healthy adult rabbits were inoculated with vaccinia virus to activate or stress the tissues. The activated skins were aseptically removed, finely cut and water was added thereto. The mixture was ground using a homogenizer to prepare an emulsion. The emulsion was filtered with pressure, and the resulting filtrate was adjusted to pH 5.0 with hydrochloric acid and heated at 100° C. with a steam flow. Proteins were removed by filtration, the filtrate was adjusted to pH 9.1 with sodium hydroxide, heated at 100° C. and filtered. The filtrate was adjusted to pH 4.1, stirred after adding 2% of activated charcoal, and the mixture was filtered to obtain a filtrate and a first batch of recovered activated charcoal. To the filtrate was added 5.5% of activated charcoal and the mixture was stirred for 2 hours, and filtered to obtain a second batch of recovered activated charcoal. The first batch of recovered activated charcoal was mixed with water, adjusted to pH 9.9 with sodium hydroxide, stirred at 60° C. for 1.5 hours and filtered. Water was then added to the first batch of the activated charcoal and to the second batch of activated charcoal. The pH of each batch was then adjusted to pH 10.9 with sodium hydroxide, and each batch was stirred at 60° C. for 1.5 hours and then filtered. The resulting filtrates were combined, neutralized with hydrochloric acid, desalted using electrodialysis with membrane (molecular weight: 100), and dried in vacuo.

Now some examples of the pharmacological test concerning the promoting action for thioredoxin production where an extract of inflamed tissues inoculated with vaccinia virus according to the present invention prepared in the above Example 1 is used as a test substance will be shown.

Pharmacological Test 1: Cytoprotective Action to Injury by Hydrogen Peroxide ($H_2O_2$)

A549 cells derived from epithelia of human pulmonary alveoli were pre-incubated for 16 hours with addition of a test substance in a DMEM medium wherefrom thiol was removed (hereinafter, said medium is a serum-free medium unless otherwise mentioned). Incubation was conducted for 6 hours more after addition of 0.3 mM $H_2O_2$ (final concentration) and, after that, LDH (lactate dehydrogenase) in the supernatant liquid of the culture was measured by an LDH assay (Roche Diagnostics) and used as an index for viability of the cells. An example of the result where a cytoprotective effect of the extract of the present invention to hydrogen peroxide injury was investigated is shown in FIG. 1.

When $H_2O_2$ stimulation was applied to the A549 cells in a serum-free medium, cell injury was resulted but, when the extract of the present invention was added and pre-cultured, the cell injury was significantly suppressed in a concentration-dependent manner. Further, a suppressive effect to the cell injury by a serum-free stimulation was also noted.

Figure 2:
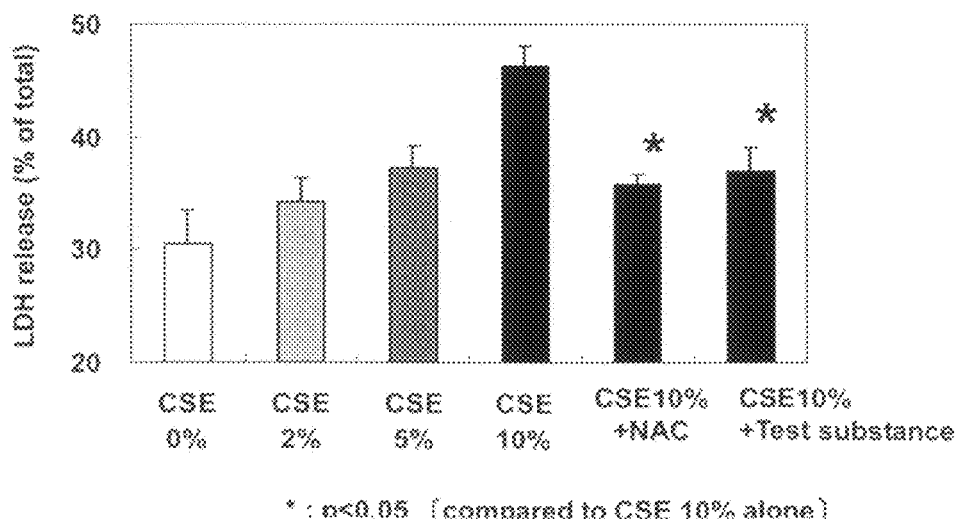
FIG. 2 is the result when a cytoprotective action of the extract of inflamed tissues inoculated with vaccinia virus according to the present invention to stimulation by cigarette smoke extract was investigated.

Pharmacological Test 2: Cytoprotective Action to Stimulation by Cigarette Smoke Extract A549 cells were pre-incubated for 16 hours with addition of a test substance (0.01 U/mL) in a DMEM medium wherefrom thiol was removed. Incubation was conducted for 6 hours more after addition of a cigarette smoke extract LDH (lactate dehydrogenase) and, after that, LDH in the supernatant liquid of the culture was measured by means of an LDH assay (Roche Diagnostics) and used as an index for viability of the cells. The cigarette smoke extract (CSE) was prepared using a cigarette smoke generator SG-200 (Shibata Kagaku). Thus, smoke of ten cigarettes (Kentucky Research Cigarette 2R4F) which was passed through 10 mL of DMEM wherefrom thiol was removed (10% HEPES was added thereto) was defined as 100% CSE and used after appropriately diluting to the concentrations which were suitable for the experiments. An example of the result where the cytoprotective effect of the extract of the present invention to stimulation by the cigarette smoke extract was investigated is shown in FIG. 2.

When the extract of the present invention was added and pre-incubated, cell injury by CSE was significantly suppressed and the resulting effect was identical with that by NAC (N-acetylcysteine, 0.1 mM).

Pharmacological Test 3: Anti-Apoptotic Action

Figure 3:
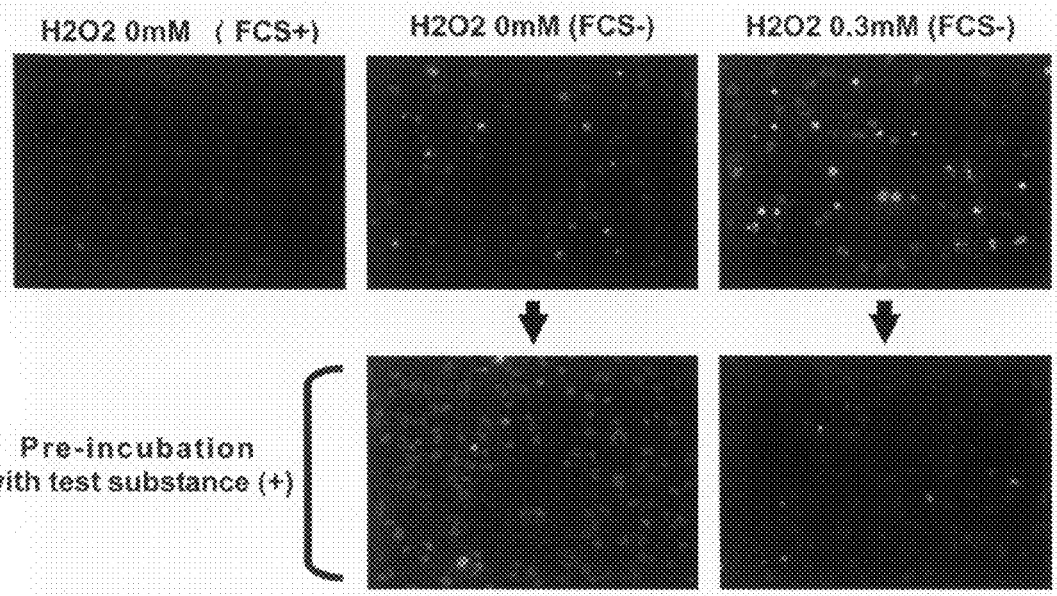
FIG. 3 is the result when an anti-apoptotic action of the extract of inflamed tissues inoculated with vaccinia virus according to the present invention to stimulation by hydrogen peroxide and serum-free stimulation was investigated.

A549 cells incubated on a Chamber slide were pre-incubated for 10 hours with addition of a test substance on a DMEM medium wherefrom thiol was removed and incubated for 20 hours more with addition of $H_2O_2$. For the sake of comparison, A549 cells were also incubated in a medium to which fetal calf serum (FCS) was added. The above was stained with Hoechst 33342 and propidium iodide and cell death was evaluated under a fluorescence microscope. An example of the result where the anti-apoptotic action of the extract of the present invention was investigated is shown in FIG. 3.

The extract of the present invention suppressed apoptosis caused by serum-free stimulation and $H_2O_2$ stimulation. (In the picture under a fluorescence microscope of FIG. 3, a cell having small and highly bright nucleus is apoptotic.)

Pharmacological Test 4: Antioxidant Action

A549 cells were pre-incubated for 16 hours with addition of a test substance (0.01 U/mL) in a DMEM medium wherefrom thiol was removed and incubated for 3 hours more with addition of 0.3 mM $H_2O_2$ (final concentration). After that, the above was treated with trypsin and then CM-H2DCFDA which is an oxidant-reactive fluorescent substrate (Molecular Probe) was added thereto followed by incubating for 20 minutes. Green fluorescence was measured by means of flow cytometry (FACSCalibur, BD Bioscience). Cells where fluorescent brightness increased by oxidant stress were defined as positive cells and the result was judged in terms of the rate of the positive cells. An example of the result where an antioxidant action of the extract of the present invention is investigated is shown in Table 1.

An increase in positive cell rate in the cells by oxidant stress such as $H_2O_2$ stimulation and serum-free was significantly suppressed by the extract of the present invention.

TABLE 1

|  | Rate of the positive cells (%) | |
| --- | --- | --- |
|  | Control | Test substance |
| Serum-free stimulation | 58 | 51 |
| $H_2O_2$ stimulation | 69 | 57 |

Pharmacological Test 5: Action for Promotion of Thioredoxin Production (Genetic Level)

Figure 4:
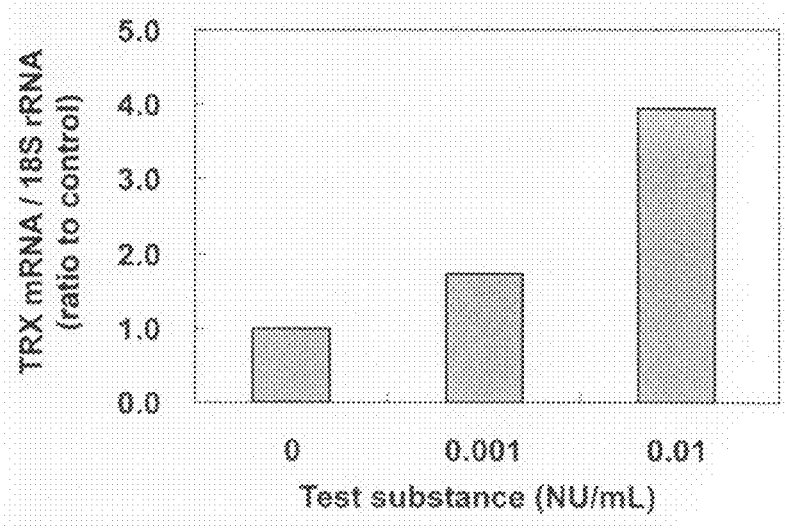
FIG. 4 is the result when a promoting action for thioredoxin (genetic level) of the extract of inflamed tissues inoculated with vaccinia virus according to the present invention was investigated.

A549 cells were incubated for 9 hours with addition of a test substance in a DMEM medium wherefrom thiol was removed. RNA was extracted and mRNA expression of thioredoxin was measured by an RT-PCR method (7300 Real Time PCR System of ABI). An example of result of investigation of promoting action of the extract of the present invention for thioredoxin production is shown in FIG. 4.

A promoting action of the extract of the present invention for thioredoxin production was noted in a concentration-dependent manner in a genetic level.

Pharmacological Test 6: Action for Promotion of Thioredoxin Production (Protein Level)

A549 cells were incubated with addition of a test substance in a DMEM medium wherefrom thiol was removed.

Figure 5:
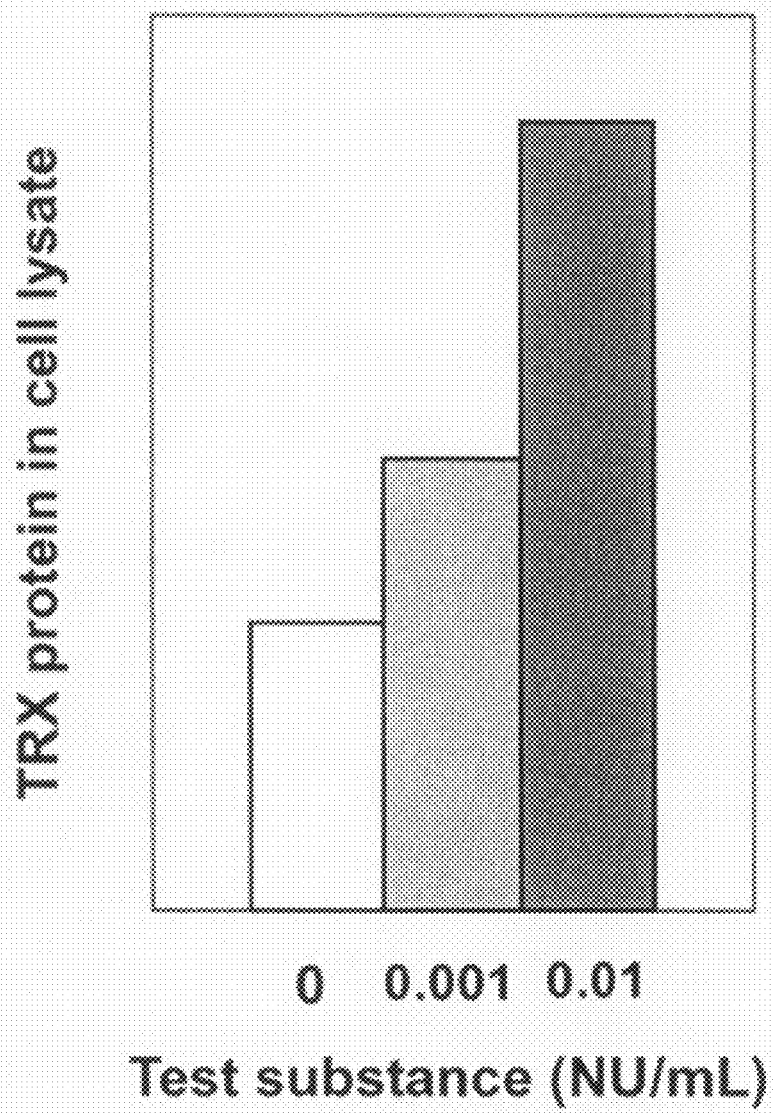
FIG. 5 is the result when a promoting action for thioredoxin (protein level) of the extract of inflamed tissues inoculated with vaccinia virus according to the present invention was investigated.
Figure 5:
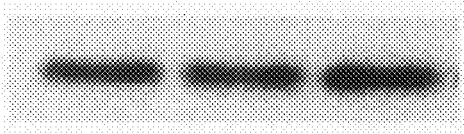

Expressed amount of thioredoxin in the product wherein cells were dissolved was measured by means of a Western blot technique. An example of the result showing an action for promotion of thioredoxin production by the extract of the present invention in a protein level is shown in FIG. 5.

A promoting action of the extract of the present invention for thioredoxin production was noted in a concentration-dependent manner in a protein level.

When WI38 which is a human lung fibroblast strain was used, the same cytoprotective action, action for promoting the thioredoxin product, etc. as in the case of A549 cells were also noted in the extract of the present invention.

Pharmacological Test 7: Tissue Protective Action (In Vivo)

Figure 6:
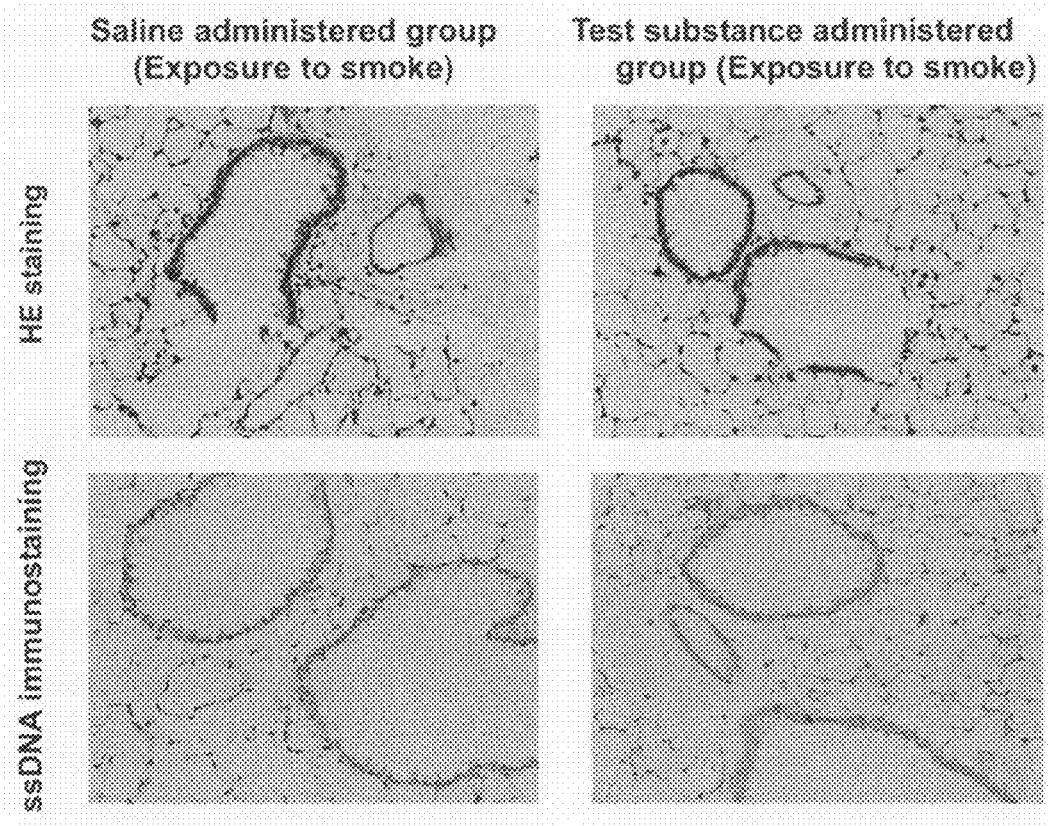
FIG. 6 is a picture under a microscope when a tissue protective action of the extract of inflamed tissues inoculated with vaccinia virus according to the present invention in pulmonary tissues of mice exposed to smoke was investigated.

Male mice (8 weeks age) of C57BL/6J strain were exposed to cigarette smoke for 3 days (day 1 to 3) and the effect by administration of a test substance (day 0 to 3; 100 NU/kg/day, i.p.) was investigated. Exposure to the smoke was conducted using a cigarette smoke generator SG-200 (Shibata Kagaku) exposing for 1 hour per day to the whole body. After 24 hours from the final exposure to the smoke, the mice were slaughtered by bleeding and made into expanded-and-fixed lung specimens using 10% neutral buffered formalin. The lung specimens were subjected to an HE staining and an ssDNA immuno-staining and inflammation and injury were evaluated. An example of the result of investigation of the tissue protective action (in vivo) of the extract of the present invention is shown in FIG. 6.

As a result of exposure to the smoke, there are induced (1) cell death of bronchiole and edema and inflammation cellular infiltration of perivascular interstitial tissue (HE staining) and (2) apoptosis of bronchiole, pulmonary alveoli and small blood vessels but, by administration of an extract of the present invention, a tendency of suppression of those pulmonary inflammations and injuries was noted. (In the picture of ssDNA immunostaining under a microscope in FIG. 6, a cell having a nucleus which is darkly stained in black is apoptotic.)

Pharmacological Test 8: Suppressive Action to Inflammatory Cell Infiltration (In Vivo)

Figure 7:
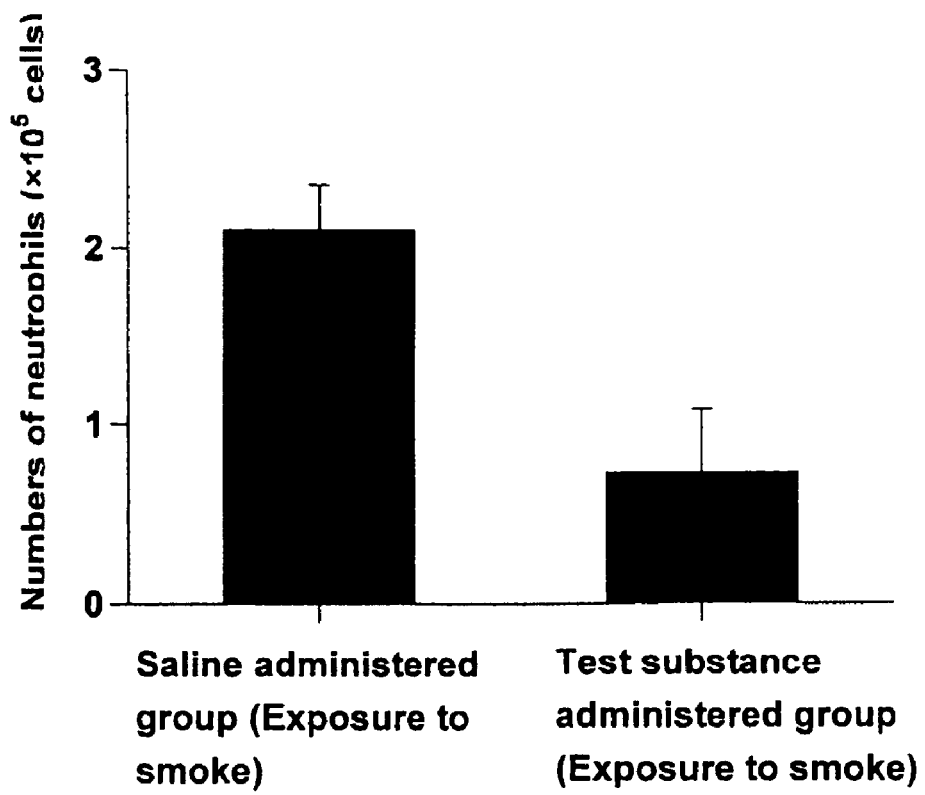
FIG. 7 is the result when inflammatory cell numbers in a washing of bronchial pulmonary alveoli of mice exposed to smoke were counted and a suppressive action for inflammatory cell infiltration by the extract of inflammatory tissues inoculated with vaccinia virus according to the present invention was investigated.

The same as in the above Pharmacological Test 7, mice of C57BL6 strain in 8 weeks age were exposed to cigarette smoke for 1 hour per day for three days using a smoke generator SG-200 (Shibata Kagaku). The mice were divided into a group to which a test substance was administered (n=3; 1 NU/kg was intraperitoneally administered 30 minutes before exposing to the smoke) and another group to which a physiological saline solution was administered (n=3). After 24 hours from the final exposure to the smoke, a bronchoalveolal lavage (BAL) was carried out and numbers of neutrophils in the BAL liquid were compared and investigated. The BAL was carried out for five times in total using 1 mL of a physiological saline solution, cytospin specimens were prepared from the resulting cells and stained with DiffQuick and cell numbers were counted. An example of the result where the suppressive action of the extract of the present invention for inflammatory cell infiltration was tested (in vivo) is shown in FIG. 7. As a result of administration of the extract of the present invention, infiltration of inflammatory cells (neutrophils) was significantly (n<0.05) suppressed.

UTILIZING POSSIBILITY IN INDUSTRY

As will be apparent from the results of the above pharmacological tests, an extract of inflamed tissues inoculated with vaccinia virus in accordance with the present invention had an excellent promotive action for thioredoxin production to oxidant stress caused by stimulation of a cigarette smoke extract, hydrogen peroxide, non-serum, etc. and also showed a significant protective action to pulmonary cells such as antioxidant action and apoptosis-suppressive action. Accordingly, an extract of inflamed tissues inoculated with vaccinia virus according to the present invention is effective for diseases and morbid states caused by imbalance of a redox state and is useful as a preventive or treating agent for chronic obstructive pulmonary diseases (COPD) where a continuous oxidant stress such as chronic smoking has been said to be a main cause. Commercially available preparations of an extract of inflamed skin of rabbits inoculated with vaccinia virus have been used for very long years and have been recognized as drugs having very high safety. As such, the extract in accordance with the present invention is a novel drug such as a promotive agent for thioredoxin production, a protective agent for pulmonary cells and a preventive and treating agent for chronic obstructive pulmonary diseases such as pulmonary emphysema and chronic bronchitis and is highly useful as a drug resulting in almost no adverse action.

The invention claimed is:

1. A method for protecting against or treating a chronic obstructive pulmonary disease comprising administering a composition consisting essentially of an effective amount of an extract of inflamed tissue inoculated with vaccinia virus to a person in need of protection against or treatment of the chronic obstructive pulmonary disease, thereby protecting against or treating the chronic obstructive pulmonary disease.

2. The method according to claim 1 wherein the inflamed tissue is skin tissue from a rabbit.

3. The method according to claim 1 wherein the composition is an injectable preparation of the extract of inflamed tissue inoculated with vaccinia virus.

4. The method according to claim 2 wherein the composition is an injectable preparation of the extract of inflamed tissue inoculated with vaccinia virus.

5. The method according to claim 1 wherein the composition is an oral preparation of the extract of inflamed tissue inoculated with vaccinia virus.

6. The method according to claim 2 wherein the composition is an oral preparation of the extract of inflamed tissue inoculated with vaccinia virus.

7. The method according to claim 1 wherein the extract of inflamed tissue inoculated with vaccinia virus is the only active ingredient present in the composition.

* * * * *